US012582732B2

(12) United States Patent
Kutzko et al.

(10) Patent No.: US 12,582,732 B2
(45) Date of Patent: Mar. 24, 2026

(54) COMPOSITION AND METHODS FOR SANITIZATION

(71) Applicant: GENZYME CORPORATION, Cambridge, MA (US)

(72) Inventors: Joseph P. Kutzko, Southborough, MA (US); Ryan F. Wollensak, Marstons Mills, MA (US)

(73) Assignee: GENZYME CORPORATION, Cambridge, MA (US)

( * ) Notice: Subject to any disclaimer, the term of this patent is extended or adjusted under 35 U.S.C. 154(b) by 936 days.

(21) Appl. No.: 17/738,760

(22) Filed: May 6, 2022

(65) Prior Publication Data

US 2022/0370653 A1     Nov. 24, 2022

Related U.S. Application Data

(60) Provisional application No. 63/185,786, filed on May 7, 2021.

(51) Int. Cl.
A61L 2/00     (2006.01)
A61L 101/34     (2006.01)
A61L 101/36     (2006.01)

(52) U.S. Cl.
CPC ........... A61L 2/0035 (2013.01); A61L 2/0088 (2013.01); *A61L 2101/34* (2020.08); *A61L 2101/36* (2020.08); *A61L 2300/254* (2013.01); *A61L 2300/404* (2013.01)

(58) Field of Classification Search
CPC ...... A61L 2/0035; A61L 2/0088; A61L 2/081; A61L 2/18; A61L 2101/34; A61L 2101/36; A61L 2300/254; A61L 2300/404; B01D 15/08; B01D 15/20; B01D 15/203; B01D 15/426; B01D 15/3809; B01J 20/285; B01J 20/3475; C07K 1/22; A01N 31/02; A01N 37/02; A01N 37/06; A01P 1/00
See application file for complete search history.

(56) References Cited

U.S. PATENT DOCUMENTS

| | | | |
|---|---|---|---|
| 9,102,709 B1 | 8/2015 | Ladiwala et al. | |
| 11,236,126 B2 * | 2/2022 | Beigie ................ | B01D 15/3809 |
| 2006/0102561 A1 | 5/2006 | Larsen et al. | |
| 2015/0093800 A1 * | 4/2015 | Mahajan .............. | B01D 15/203 |
| | | | 530/416 |

(Continued)

FOREIGN PATENT DOCUMENTS

WO     9611572 A1     4/1996
WO     2015035180 A1     3/2015
(Continued)

OTHER PUBLICATIONS

Millipore Sigma, webpage titled "Sodium Acetate Buffer Solution for Molecular Biology", 2025 (Year: 2025).*

(Continued)

*Primary Examiner* — Jennifer Wecker
*Assistant Examiner* — Brady C Pilsbury
(74) *Attorney, Agent, or Firm* — MH2 Technology Law Group, LLP

(57) ABSTRACT

The present technology relates to a novel sanitization method for chromatography media and supporting equipment comprising treatment with a sanitization/sterilization solution comprising acetic acid and hexylene glycol.

21 Claims, 6 Drawing Sheets

| | E. Coli ATCC 10536 | | | | | S. Aureus ATCC 6538 | | | | | O. Anthropi | | | | | B. Cereus/thuringiensis | | | | |
|---|---|---|---|---|---|---|---|---|---|---|---|---|---|---|---|---|---|---|---|---|
| Log10 Concentration To Control: | 5.224 | | | | | 4.498 | | | | | 5.279 | | | | | 3.752 | | | | |
| | T10 | T20 | T30 | T60 | 1 Week | T10 | T20 | T30 | T60 | 1 Week | T10 | T20 | T30 | T60 | 1 Week | T10 | T20 | T30 | T60 | 1 Week |
| 0.1M NaOH | >5.22 | >5.22 | >5.22 | >5.22 | | >4.50 | >4.50 | >4.50 | >4.50 | | >5.28 | >5.28 | >5.28 | >5.28 | | <0.57 | <0.57 | <0.57 | <0.57 | |
| 0.5M NaOH | >5.22 | >5.22 | >5.22 | >5.22 | | >4.50 | >4.50 | >4.50 | >4.50 | | >5.28 | >5.28 | >5.28 | >5.28 | | <0.57 | <0.57 | <0.57 | <0.57 | |
| 0.1M NaOH, 25% Hexylene Glycol | >5.22 | >5.22 | >5.22 | >5.22 | | >4.50 | >4.50 | >4.50 | >4.50 | | 4.28 | >5.28 | >5.28 | >5.28 | | <0.57 | <0.57 | <0.57 | <0.57 | |
| 0.1M NaOH, 40% Hexylene Glycol | >5.22 | >5.22 | >5.22 | >5.22 | | >4.50 | >4.50 | >4.50 | >4.50 | | >5.28 | >5.28 | >5.28 | >5.28 | | <0.57 | <0.57 | <0.57 | <0.57 | |
| 40% Isopropanol, 0.1M NaOH | >5.22 | >5.22 | >5.22 | >5.22 | | >4.50 | >4.50 | >4.50 | >4.50 | | >5.28 | >5.28 | >5.28 | >5.28 | | <0.57 | <0.57 | <0.57 | <0.57 | |
| 0.1M NaOH, 1% Tween80 | >5.22 | >5.22 | >5.22 | >5.22 | | >4.50 | >4.50 | >4.50 | >4.50 | | >5.28 | >5.28 | >5.28 | >5.28 | | 1.64 | 1.27 | 1.34 | 1.47 | |
| 0.1M NaOH, 5% Tween80 | >5.22 | >5.22 | >5.22 | >5.22 | | >4.50 | >4.50 | >4.50 | >4.50 | | >5.28 | >5.28 | >5.28 | >5.28 | | 2.15 | 2.45 | 2.27 | 2.46 | |

| | E. Coli ATCC 10536 | | | | S. Aureus ATCC 6538 | | | | O. Anthropi | | | | B. Cereus/thuringiensis | | | | P. Chrysogenum ATCC 11709 | | | | C. Herbarum Cladosporoides/M. Aronci | | | |
|---|---|---|---|---|---|---|---|---|---|---|---|---|---|---|---|---|---|---|---|---|---|---|---|---|
| Log10 Concentration To Control: | 5.254 | | | | 4.895 | | | | 4.971 | | | | 3.944 | | | | 4.732 | | | | 4.866 | | | |
| | T20 | T40 | T60 | T24H | T20 | T40 | T60 | T24H | T20 | T40 | T60 | T24H | T20 | T40 | T60 | T24H | T20 | T40 | T60 | T24H | T20 | T40 | T60 | T24h |
| 65mM Acetic Acid, 20% Hexylene Glycol | >5.25 | >5.25 | >5.25 | >5.25 | >4.89 | >4.89 | >4.89 | >4.89 | >4.97 | >4.97 | >4.97 | >4.97 | 2.64 | >3.94 | >3.94 | >3.94 | >4.73 | >4.73 | >4.73 | >4.73 | 3.57 | 3.87 | >4.87 | >4.87 |
| 200mM Acetic Acid, 0.5% Tween80 | 2.07 | 2.18 | 2.31 | >5.25 | >4.89 | >4.89 | >4.89 | >4.89 | <1.79 | <1.79 | 3.07 | >4.97 | 2.64 | 2.46 | 2.46 | 2.91 | 3.13 | 3.43 | 3.73 | >4.73 | 3.25 | 3.57 | 3.87 | >4.87 |
| 150mM Acetic Acid, 100mM Phosphoric Acid, 5% Tween80 | >5.25 | >5.25 | >5.25 | >5.25 | >4.89 | >4.89 | >4.89 | >4.89 | >4.97 | >4.97 | >4.97 | >4.97 | 2.46 | >3.94 | >3.94 | >3.94 | 3.73 | >4.73 | >4.73 | >4.73 | 3.39 | >4.87 | >4.87 | >4.87 |

(56) References Cited

U.S. PATENT DOCUMENTS

| 2015/0183821 | A1* | 7/2015 | Konstantinov | C07K 16/00 |
| | | | | 435/69.6 |
| 2019/0233468 | A1* | 8/2019 | Beigie | C07K 16/00 |

FOREIGN PATENT DOCUMENTS

| WO | 2016139128 | A1 | 9/2016 |
| WO | 2018140887 | A1 | 8/2018 |

OTHER PUBLICATIONS

"PAB—An Enhanced Sanitization Option for ProSep Protein A Affinity Chromatography Media", Technical Brief, Merck Millipore, 2014.

* cited by examiner

Cycle #

Top table

| Log10 Concentration To Control: | E. Coli ATCC 10536 (5.224) | | | | | S. Aureus ATCC 6538 (4.498) | | | | | O. Anthropi (5.279) | | | | | B. Cereus/thuringiensis (3.752) | | | | |
|---|---|---|---|---|---|---|---|---|---|---|---|---|---|---|---|---|---|---|---|---|
| | T10 | T20 | T30 | T60 | 1Week | T10 | T20 | T30 | T60 | 1Week | T10 | T20 | T30 | T60 | 1Week | T10 | T20 | T30 | T60 | 1Week |
| 0.1M NaOH | >5.22 | >5.22 | >5.22 | >5.22 | | >4.50 | >4.50 | >4.50 | >4.50 | | >5.28 | >5.28 | >5.28 | >5.28 | | <0.57 | <0.57 | <0.57 | <0.57 | |
| 0.5M NaOH | >5.22 | >5.22 | >5.22 | >5.22 | | >4.50 | >4.50 | >4.50 | >4.50 | | >5.28 | >5.28 | >5.28 | >5.28 | | | <0.57 | <0.57 | <0.57 | |
| 0.1M NaOH, 25% Hexylene Glycol | >5.22 | >5.22 | >5.22 | >5.22 | | >4.50 | >4.50 | >4.50 | >4.50 | | 4.28 | >5.28 | >5.28 | >5.28 | | <0.57 | <0.57 | <0.57 | <0.57 | |
| 0.1M NaOH, 40% Hexylene Glycol | >5.22 | >5.22 | >5.22 | >5.22 | | >4.50 | >4.50 | >4.50 | >4.50 | | >5.28 | >5.28 | >5.28 | >5.28 | | | <0.57 | <0.57 | <0.57 | |
| 40% Isopropanol, 0.1M NaOH | >5.22 | >5.22 | >5.22 | >5.22 | | >4.50 | >4.50 | >4.50 | >4.50 | | >5.28 | >5.28 | >5.28 | >5.28 | | <0.57 | <0.57 | <0.57 | <0.57 | |
| 0.1M NaOH, 1% Tween80 | >5.22 | >5.22 | >5.22 | >5.22 | | >4.50 | >4.50 | >4.50 | >4.50 | | >5.28 | >5.28 | >5.28 | >5.28 | | 1.64 | 1.27 | 1.34 | 1.47 | |
| 0.1M NaOH, 5% Tween80 | >5.22 | >5.22 | >5.22 | >5.22 | | >4.50 | >4.50 | >4.50 | >4.50 | | >5.28 | >5.28 | >5.28 | >5.28 | | 2.15 | 2.45 | 2.27 | 2.45 | |

Bottom table

| Log10 Concentration To Control: | E. Coli ATCC 10536 (5.254) | | | | S. Aureus ATCC 6538 (4.895) | | | | O. Anthropi (4.971) | | | | B. Cereus/thuringiensis (3.944) | | | | P. Chrysogenum ATCC 11709 (4.732) | | | | C. Herbarum/Cladosporoides/M. Aronci (4.866) | | | |
|---|---|---|---|---|---|---|---|---|---|---|---|---|---|---|---|---|---|---|---|---|---|---|---|---|
| | T20 | T40 | T60 | T24H | T20 | T40 | T60 | T24H | T20 | T40 | T60 | T24H | T20 | T40 | T60 | T24H | T20 | T40 | T60 | T24H | T20 | T40 | T60 | T24h |
| 65mM Acetic Acid, 20% Hexylene Glycol | >5.25 | >5.25 | >5.25 | >5.25 | >4.89 | >4.89 | >4.89 | >4.89 | >4.97 | >4.97 | >4.97 | >4.97 | 2.64 | >3.94 | >3.94 | >3.94 | >4.73 | >4.73 | >4.73 | >4.73 | 3.57 | 3.87 | >4.87 | >4.87 |
| 200mM Acetic Acid, 0.5% Tween80 | 2.07 | 2.16 | 2.31 | >5.25 | >4.89 | >4.89 | >4.89 | >4.89 | <1.79 | <1.79 | 3.07 | >4.97 | 2.64 | 2.46 | 2.46 | 2.91 | 3.13 | 3.43 | 3.73 | >4.73 | 3.26 | 3.57 | 3.87 | >4.87 |
| 150mM Acetic Acid, 100mM Phosphoric Acid, 5% Tween80 | >5.25 | >5.25 | >5.25 | >5.25 | >4.89 | >4.89 | >4.89 | >4.89 | >4.97 | >4.97 | >4.97 | >4.97 | 2.46 | >3.94 | >3.94 | >3.94 | 3.73 | >4.73 | >4.73 | >4.73 | 3.39 | >4.87 | >4.87 | >4.87 |

FIG. 4

COMPOSITION AND METHODS FOR SANITIZATION

CROSS REFERENCE TO RELATED APPLICATIONS

The present application claims priority from U.S. Provisional Application 63/185,786, filed on May 7, 2021. The content of the aforementioned provisional application is incorporated herein by reference in its entirety.

BACKGROUND

The high commercial demand for biologics has led to pharmaceutical companies placing an emphasis on maximizing productivity and product quality whilst controlling costs associated with manufacturing. This push for increased efficiency has allowed affinity chromatography to rise to the forefront as it provides highly specific binding and reduces the overall number of steps required to purify an analyte of interest from a crude mixture. Affinity chromatography resins provide improved yields and purity standards when compared to traditional purification techniques.

Any bioprocess chromatography application, including affinity chromatography, requires a high degree of control over contaminant and impurity removal. These contaminants include, but are not limited to, proteins, carbohydrates, lipids, lipopolysaccharides (e.g., endotoxins), lipoproteins, nucleic acids, and/or microbial species. Macromolecular impurities, e.g., proteins, carbohydrates, lipids, nucleic acids, etc., are often addressed by taking advantage of various intermolecular forces and separating out the target analyte from impurities during wash and elution phases of the chromatography operation. Microbial contamination, however, poses an exceptional threat to any chromatography operation due to its ability to proliferate during the extended resin lifetime associated with modern manufacturing. In fact, microbial contamination poses an even higher risk in processes where the chromatography step is integrated into the bioreactor for continuous capture.

Traditionally, chromatography resin decontamination methods include treatment with sodium hydroxide and/or gamma irradiation. However, affinity resins (e.g., resins conjugated to peptide-based ligands) are not as stable when exposed to sodium hydroxide or gamma irradiation.

SUMMARY

In one aspect, the present disclosure provides methods for sanitizing or sterilizing chromatography media and/or supporting equipment, comprising contacting the chromatography media and/or supporting equipment with a sanitization or sterilization solution comprising a carboxylic acid and about 20% hexylene glycol, wherein the concentration of the carboxylic acid is from about 40 mM to about 200 mM.

In another aspect, the present disclosure provides methods for eluting a target analyte bound to chromatography media, comprising contacting the chromatography media with an elution buffer solution comprising a carboxylic acid and about 20% hexylene glycol, wherein the concentration of the carboxylic acid is from about 40 mM to about 200 mM.

In another aspect, the present disclosure provides methods for sanitizing or sterilizing chromatography media and/or supporting equipment, comprising contacting the chromatography media and/or supporting equipment with a sanitization or sterilization solution comprising a carboxylic acid and hexylene glycol, such that the pH of this solution is ≤3.5, wherein this method provides a high degree of bacteria, spore, and/or mold inactivation or killing within 1 hour of treatment with the solution.

In another aspect, the present disclosure provides methods for eluting a target analyte bound to chromatography media, comprising contacting the chromatography media with an elution buffer solution comprising a carboxylic acid and hexylene glycol, such that the pH of this solution is ≤3.5, wherein the method provides improved product yield and peak sharpness.

In another aspect, the present disclosure provides methods for increasing the lifetime of a chromatography media, comprising sanitizing or sterilizing the chromatography media with a solution comprising about 65 mM acetic acid and about 20% hexylene glycol, wherein the method allows the lifetime of the chromatography media to be increased by at least about 10% compared to sanitizing or sterilizing the chromatography media with at least one of: (i) gamma irradiation or (ii) a buffer comprising sodium hydroxide.

In yet another aspect, the present disclosure provides solutions comprising 65 mM acetic acid and 20% hexylene glycol.

In some embodiments, the carboxylic acid is of the formula $R^1$—C(=O)—OH, wherein $R^1$ is substituted or unsubstituted $C_1$-$C_{12}$ alkyl, alkenyl, or alkynyl. In some embodiments, the carboxylic acid is acetic acid. In some embodiments, the concentration of acetic acid is 40-200 mM. In some embodiments, the concentration of acetic acid is 65 mM. In some embodiments, the concentration of hexylene glycol is 8-80%. In some embodiments, the concentration of hexylene glycol is 20%.

In some embodiments, the chromatography is affinity chromatography.

In some embodiments, the affinity ligand is based on protein A or any variant thereof. In some embodiments, the affinity ligand is based on native protein A. In some embodiments, the affinity ligand is based on recombinant protein A. In some embodiments, the affinity ligand is based on genetically engineered protein A. In some embodiments, the affinity ligand is based on artificial protein A.

In some embodiments, the affinity ligand is based on protein G or any variant thereof. In some embodiments, the affinity ligand is based on protein A/G or any variant thereof. In some embodiments, the affinity ligand is based on protein L or any variant thereof.

In some embodiments, the pH of the sanitization solution is between 3.0 and 3.5. In some embodiments, the pH of the sanitization solution is 3.1.

In some embodiments, the bacteria, spore, and/or mold inactivation is achieved within 40 minutes of treatment with the sanitization solution.

In some embodiments, the sanitization method is used toward the purification of a polypeptide. In some embodiments, the polypeptide is an antibody. In some embodiments, the antibody is a monoclonal antibody.

In some embodiments, the polypeptide is a recombinant enzyme. In some embodiments, the recombinant enzyme is a human recombinant enzyme. In some embodiments, the recombinant enzyme is a lysosomal glycogen-specific enzyme. In some embodiments, the recombinant enzyme is a human enzyme acid α-glucosidase (GAA). In some embodiments, the recombinant enzyme is Myozyme®.

BRIEF DESCRIPTION OF THE FIGURES

FIG. 4 is a table showing results of the microbial kill study described in Example 4.

DETAILED DESCRIPTION

Figure 1:
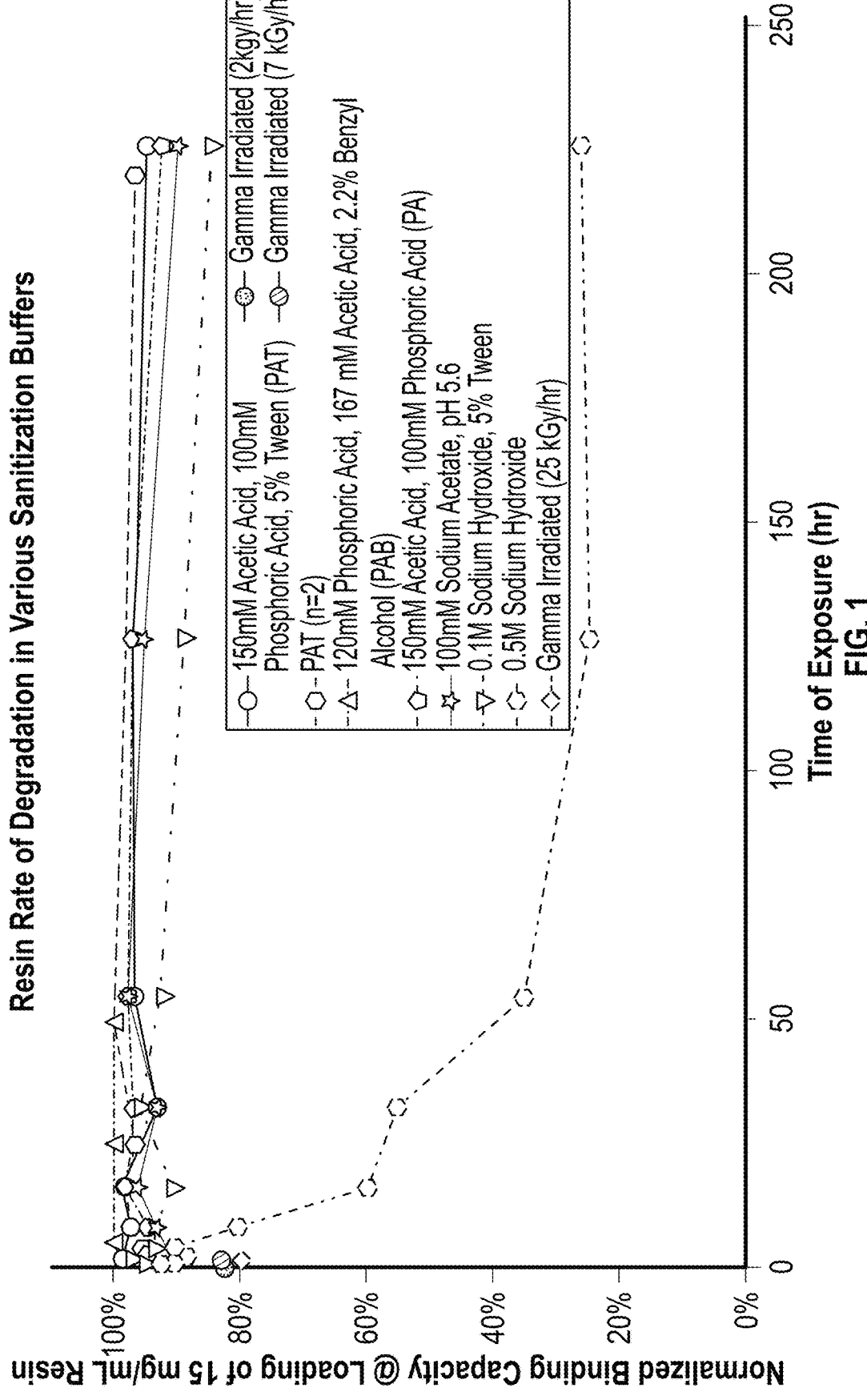
FIG. 1 is a plot depicting the impact of various sanitization methods on the binding capacity of affinity chromatography resin.

Features, objects, and advantages of the present technology are apparent in the detailed description that follows. It should be understood, however, that the detailed description, while indicating embodiments and aspects of the present technology, is given by way of illustration only, not limitation. Various changes and modification within the scope of the present technology will become apparent to those skilled in the art from the detailed description.

The definitions of certain terms as used in this specification are provided below. Unless defined otherwise, all technical and scientific terms used herein generally have the same meaning as commonly understood by one of ordinary skill in the art to which this present technology belongs.
Definitions The moieties described below can be substituted or unsubstituted. "Substituted" refers to replacement of a hydrogen atom of a molecule or an R-group with one or more additional R-groups such as deuterium, halogen, alkyl, haloalkyl, alkenyl, alkoxy, alkoxyalkyl, alkylthio, trifluoromethyl, acyloxy, hydroxy, hydroxyalkyl, mercapto, carboxy, cyano, acyl, aryloxy, aryl, arylalkyl, heteroaryl, amino, aminoalkyl, alkylamino, dialkylamino, morpholino, piperidino, pyrrolidin-1-yl, piperazin-1-yl, nitro, phosphine, phosphinate, phosphonate, sulfate, $=O$, $=S$, or other R-groups. Unless otherwise indicated, an optionally substituted group may have a substituent at each substitutable position of a group. Combinations of substituents contemplated herein are preferably those that result in the formation of stable (e.g., not substantially altered for a week or longer when kept at a temperature of 40° C. or lower in the absence of moisture or other chemically reactive conditions), or chemically feasible, compounds.

Unless specified otherwise, the term "carboxylic acid" as used herein refers to a compound of formula $R^1$—C(=O)—OH, wherein $R^1$ is hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio. In some embodiments, the carboxylic acid is selected from the group consisting of acetic acid, citric acid, succinic acid, and formic acid.

Unless specified otherwise, the term "glycol" as used herein refers to a compound of formula $(R^2)(R^3)$—C(OH)—C(OH)—$(R^4)(R^5)$, wherein $R^2$, $R^3$, $R^4$, and $R^5$ are each, independently, hydrogen, deuterium, halo, amino, hydroxy, cyano, formyl, furyl, nitro, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, halothiocarbonylthio, and —$S(O)_nR_{11}$ (n=0 to 2, $R_{11}$ is directly connected to S), wherein $R_{11}$ is selected from the group consisting of hydrogen, deuterium, halo, amino, hydroxy, thiol, cyano, formyl, alkyl, haloalkyl, alkenyl, haloalkenyl, alkynyl, haloalkynyl, acyloxy, alkoxy, haloalkoxy, thioalkoxy, halothioalkoxy, alkanoyl, haloalkanoyl, thioalkanoyl, halothioalkanoyl, carboxy, carbonyloxy, halocarbonyloxy, carbonylthio, halocarbonylthio, thiocarbonyloxy, halothiocarbonyloxy, thiocarbonylthio, and halothiocarbonylthio.

The term "sanitization" as used herein refers to the process of reducing and/or inactivating microbial contamination in a given environment. In some embodiments, sanitization according to the present disclosure can comprise inactivation of microbes that may contaminate the chromatographic media and/or supporting equipment. In some embodiments, the methods described herein are considered as microbiostatic.

The term "sterilization" as used herein refers to the process of destroying or eliminating all microorganisms in a given environment. In some embodiments, sterilization is the complete elimination of microbes that may contaminate the chromatographic media and/or supporting equipment. In some embodiments, sterilization is a greater than 6 log reduction of microbes that may contaminate the chromatographic media and/or supporting equipment. In some embodiments, the methods described herein are considered as microbiocidal.

The term "inactivation" as used herein refers to any process that reduces or inhibits microbial replication.

The term "killing" as used herein refers to any method that causes permanent ending of vital cellular processes such that the cell can no longer survive or reproduce. The term "complete kill" as used herein refers to a situation wherein when a culture is inoculated in a sterilization solution, allowed to incubate (killing occurs), and then plated in a favorable environment for microbial growth, nothing grows, thereby indicating that no organism in the original spike survived exposure to the sterilization solution.

The term "variant" as used herein encompasses any form of a particular protein that is recombinantly expressed in a host cell or non-native host cell. In some embodiments, the term "variant" refers to a protein recombinantly expressed from its native DNA sequence. In some embodiments, the term "variant" refers to a protein recombinantly expressed from a codon optimized DNA sequence. In some embodiments, the term "variant" refers to a recombinantly expressed full-length protein. In some embodiments, the term "variant" refers to a recombinantly expressed truncated form of the protein. In some embodiments, the term "variant" refers to a recombinantly expressed mutant protein. In some embodiments, the mutant protein contains point mutations at one or more positions in its amino acid sequence. In some embodiments, the term "variant" refers to a recombinantly expressed engineered protein, e.g., a genetically engineered protein. In some embodiments, the term "variant" refers to a recombinantly expressed artificial protein.

Sanitization/Sterilization Solution

In some embodiments, the present technology relates to a sanitization or sterilization solution comprising a carboxylic acid and a glycol.

In some embodiments, the present technology relates to a sanitization or sterilization solution comprising acetic acid. In some embodiments, the solution comprises about 40-200 mM acetic acid. In some embodiments, the solution comprises about 40-200 mM, about 50-190 mM, about 60-180 mM, about 70-170 mM, about 80-160 mM, about 90-150 mM, about 100-140 mM, or about 110-130 mM acetic acid. In some embodiments, the solution comprises about 40, 50, 60, 70, 80, 90, 100, 110, 120, 130, 140, or 150 (or any number between any two of the preceding values) mM acetic acid. In some embodiments, the solution comprises about 65 mM acetic acid.

In some embodiments, the present technology relates to a sanitization or sterilization solution comprising hexylene glycol. In some embodiments, the solution comprises about 8-80% hexylene glycol. In some embodiments, the solution comprises about 10-70%, about 12-60%, about 14-50%, about 16-40%, about 18-30%, or about 20-25% hexylene glycol. In some embodiments, the solution comprises about 8%, 10%, 12%, 14%, 16%, 18%, 20%, 25%, 30%, 40%, 50%, 60%, 70%, or 80% hexylene glycol. In some embodiments, the solution comprises about 20% hexylene glycol.

In some embodiments, the present technology relates to a sanitization or sterilization solution comprising acetic acid and hexylene glycol. In some embodiments, the present technology relates to a sanitization or sterilization solution comprising about 40-200 mM acetic acid and about 8-80% hexylene glycol, about 50-190 mM acetic acid and about 10-70% hexylene glycol, about 60-180 mM acetic acid and about 12-60% hexylene glycol, about 70-170 mM acetic acid and about 14-50% hexylene glycol, about 80-160 mM acetic acid and about 16-40% hexylene glycol, about 90-150 mM acetic acid and about 18-30% hexylene glycol, about 100-140 mM acetic acid and about 20-25% hexylene glycol, or about 110-130 mM acetic acid and about 20-25% hexylene glycol.

In some embodiments, the present technology relates to a sanitization or sterilization solution comprising about 40 mM acetic acid and about 8% hexylene glycol, about 50 mM acetic acid and about 10% hexylene glycol, about 60 mM acetic acid and about 12% hexylene glycol, about 70 mM acetic acid and about 14% hexylene glycol, about 80 mM acetic acid and about 16% hexylene glycol, about 90 mM acetic acid and about 18% hexylene glycol, about 100 mM acetic acid and about 20% hexylene glycol, about 110 mM acetic acid and about 25% hexylene glycol, about 120 mM acetic acid and about 30% hexylene glycol, about 130 mM acetic acid and about 40% hexylene glycol, about 140 mM acetic acid and about 50% hexylene glycol, about 150 mM acetic acid and about 60% hexylene glycol, about 160 mM acetic acid and about 70% hexylene glycol, about 170 mM acetic acid and about 80% hexylene glycol, about 180 mM acetic acid and about 80% hexylene glycol, about 190 mM acetic acid and about 80% hexylene glycol, or about 200 mM acetic acid and about 80% hexylene glycol. In some embodiments, the present technology relates to a sanitization or sterilization solution comprising about 65 mM acetic acid and about 20% hexylene glycol.

In some embodiments, the present technology relates to a sanitization or sterilization solution with a pH of about 3.5. In some embodiments, the solution has a pH of about 3.4, about 3.3, about 3.2, or about 3.1, or about 3.0, or about 2.9. In some embodiments, the solution has a pH of about 3.0.

In some embodiments, the solution comprises about 65 mM acetic acid and about 20% hexylene glycol and has a pH of about 3.0.

Methods of Sanitization/Sterilization

In some embodiments, the present disclosure provides a sanitization or sterilization method for chromatography media and/or supporting equipment comprising treatment with a sanitization or sterilization solution comprising a carboxylic acid and a glycol. The potential microbial contaminants addressed by the present technology include, without limitation, viruses, bacteria, fungi, and parasites. In some embodiments, the present method provides a high degree of bacteria, spore, and/or mold inactivation or killing.

In some embodiments, the microbial contaminant is a virus, e.g., a DNA virus, a RNA virus, an enveloped virus, or a non-enveloped virus. Nonlimiting examples of viral contaminants include human immunodeficiency virus (HIV), hepatitis viruses, human herpes viruses, cytomegalovirus, Epstein-Barr virus, and West Nile virus. In some embodiments, the microbial contaminant is bacteria, e.g., gran-negative bacteria, gram-positive bacteria, and/or biofilm-forming bacteria. Nonlimiting examples of bacterial contaminants include *Treponema pallidum, Neisseria gonorrhoea, Chlamydia trachomatis, Streptococcus pyogenes, Mycobacterium tuberculosis, Brucella melitensis, Brucella melitensis, Ehrlichia, Staphylococci, Streptococci,* and *Pseudomonas aeruginosa.* In some embodiments, the microbial contaminant is fungi. Nonlimiting examples of fungal contaminants include *Aspergillus, Penicillium, Fusarium,* and *Alternaria.* In some embodiments, the microbial contaminant is a parasite. Nonlimiting examples of parasitic contaminants include *Amoeba, Plasmodium, Trypanosoma cruzi* and *Babesia microti.*

In some embodiments, the present disclosure relates to a method of sanitizing or sterilizing chromatographic media and/or supporting equipment by contacting the media and/or equipment with a sanitization or sterilization solution described in the present disclosure. In some embodiments, the sanitization or sterilization solution comprises a carboxylic acid and a glycol.

In some embodiments, the present technology relates to a method of sanitizing or sterilizing chromatographic media and/or supporting equipment by contacting the media and/or equipment with a sanitization or sterilization solution comprising acetic acid. In some embodiments, the solution comprises about 40-200 mM acetic acid. In some embodiments, the solution comprises about 40-200 mM, about 50-190 mM, about 60-180 mM, about 70-170 mM, about 80-160 mM, about 90-150 mM, about 100-140 mM, or about 110-130 mM acetic acid. In some embodiments, the solution comprises about 40, 50, 60, 70, 80, 90, 100, 110, 120, 130, 140, or 150 (or any number between any two of the preceding values) mM acetic acid. In some embodiments, the solution comprises about 65 mM acetic acid.

In some embodiments, the present technology relates to a method of sanitizing or sterilizing chromatographic media and/or supporting equipment by contacting the media and/or equipment with a sanitization or sterilization solution comprising hexylene glycol. In some embodiments, the solution comprises about 8-80% hexylene glycol. In some embodiments, the solution comprises about 10-70%, about 12-60%, about 14-50%, about 16-40%, about 18-30%, or about 20-25% hexylene glycol. In some embodiments, the solution comprises about 8%, 10%, 12%, 14%, 16%, 18%, 20%, 25%, 30%, 40%, 50%, 60%, 70%, or 80% hexylene glycol. In some embodiments, the solution comprises about 20% hexylene glycol.

In some embodiments, the present technology relates to a method of sanitizing or sterilizing chromatographic media and/or supporting equipment by contacting the media and/or equipment with a sanitization or sterilization solution comprising acetic acid and hexylene glycol. In some embodiments, the solution comprises about 40-200 mM acetic acid and about 8-80% hexylene glycol, about 50-190 mM acetic acid and about 10-70% hexylene glycol, about 60-180 mM acetic acid and about 12-60% hexylene glycol, about 70-170 mM acetic acid and about 14-50% hexylene glycol, about 80-160 mM acetic acid and about 16-40% hexylene glycol, about 90-150 mM acetic acid and about 18-30% hexylene glycol, about 100-140 mM acetic acid and about 20-25% hexylene glycol, or about 110-130 mM acetic acid and about 20-25% hexylene glycol.

In some embodiments, the present technology relates to a method of sanitizing or sterilizing chromatographic media and/or supporting equipment by contacting the media and/or equipment with a sanitization or sterilization solution comprising about 40 mM acetic acid and about 8% hexylene glycol, about 50 mM acetic acid and about 10% hexylene glycol, about 60 mM acetic acid and about 12% hexylene glycol, about 70 mM acetic acid and about 14% hexylene glycol, about 80 mM acetic acid and about 16% hexylene glycol, about 90 mM acetic acid and about 18% hexylene glycol, about 100 mM acetic acid and about 20% hexylene glycol, about 110 mM acetic acid and about 25% hexylene glycol, about 120 mM acetic acid and about 30% hexylene glycol, about 130 mM acetic acid and about 40% hexylene glycol, about 140 mM acetic acid and about 50% hexylene glycol, about 150 mM acetic acid and about 60% hexylene glycol, about 160 mM acetic acid and about 70% hexylene glycol, about 170 mM acetic acid and about 80% hexylene glycol, about 180 mM acetic acid and about 80% hexylene glycol, about 190 mM acetic acid and about 80% hexylene glycol, or about 200 mM acetic acid and about 80% hexylene glycol. In some embodiments, the solution comprises about 65 mM acetic acid and about 20% hexylene glycol.

In some embodiments, the present technology relates to a method of sanitizing or sterilizing chromatographic media and/or supporting equipment by contacting the media and/or equipment with a sanitization or sterilization solution that has a pH of about 3.5. In some embodiments, the solution has a pH of about 3.4, about 3.3, about 3.2, or about 3.1, about 3.0, or about 2.9. In some embodiments, the solution has a pH of about 3.0.

In some embodiments, a sanitization solution of the present disclosure inactivates all vegetative, biofilm-forming, spore-forming, and/or mold-forming microbes (e.g., viruses, bacteria, fungi, parasites, etc.) within about 10 hours of treatment with this solution. In some embodiments, a sanitization solution of the present disclosure inactivates all vegetative, biofilm-forming, spore-forming, and/or mold-forming microbes within about 0-10 hours, about 0-9 hours, about 0-8 hours, about 0-7 hours, about 0-6 hours, about 0-5 hours, about 0-4 hours, about 0-3 hours, about 0-2 hours, or about 0-1 hour of treatment with the solution. In some embodiments, a sanitization solution of the present disclosure inactivates all vegetative, biofilm-forming, spore-forming, and/or mold-forming microbes in about 10 hours, about 9 hours, about 8 hours, about 7 hours, about 6 hours, about 5 hours, about 4 hours, about 3 hours, about 2 hours, or about 1 hour of treatment with the solution. In some embodiments, a sanitization solution of the present disclosure inactivates all vegetative, biofilm-forming, spore-forming, and/or mold-forming microbes in about 10 minutes, about 20 minutes, about 30 minutes, about 40 minutes, about 50 minutes, about 60 minutes, about 70 minutes, about 80 minutes, about 90 minutes of treatment with the solution. In some embodiments, a sanitization solution of the present disclosure inactivates all vegetative, biofilm-forming, spore-forming, and/or mold-forming microbes within about 40 minutes of treatment with this solution. In some embodiments, the present sanitization method is sufficient to allow the sanitized media and/or equipment to be subsequently utilized in the detection, purification, and/or preparation of materials for therapeutic administration.

In some embodiments, a sterilization solution of the present disclosure kills all vegetative, biofilm-forming, spore-forming, and/or mold-forming microbes (e.g., viruses, bacteria, fungi, parasites, etc.) within about 10 hours of treatment with this solution. In some embodiments, a sterilization solution of the present disclosure kills all vegetative, biofilm-forming, spore-forming, and/or mold-forming microbes within about 0-10 hours, about 0-9 hours, about 0-8 hours, about 0-7 hours, about 0-6 hours, about 0-5 hours, about 0-4 hours, about 0-3 hours, about 0-2 hours, or about 0-1 hour of treatment with the solution. In some embodiments, a sterilization solution of the present disclosure kills all vegetative, biofilm-forming, spore-forming, and/or mold-forming microbes in about 10 hours, about 9 hours, about 8 hours, about 7 hours, about 6 hours, about 5 hours, about 4 hours, about 3 hours, about 2 hours, or about 1 hour of treatment with the solution. In some embodiments, a sterilization solution of the present disclosure kills all vegetative, biofilm-forming, spore-forming, and/or mold-forming microbes in about 10 minutes, about 20 minutes, about 30 minutes, about 40 minutes, about 50 minutes, about 60 minutes, about 70 minutes, about 80 minutes, about 90 minutes of treatment with the solution. In some embodiments, a sterilization solution of the present disclosure kills all vegetative, biofilm-forming, spore-forming, and/or mold-forming microbes within about 40 minutes of treatment with this solution. In some embodiments, the present sterilization method is sufficient to allow the sterilized media and/or equipment to be subsequently utilized in the detection, purification, and/or preparation of materials for therapeutic administration.

In some embodiments, the chromatographic media and/or supporting equipment is exposed to a sanitization or sterilization solution of the present disclosure at a temperature from about 0° C. to about 40° C. In some embodiments, the chromatographic media and/or supporting equipment is exposed to the solution at a temperature from about 0° C. to about 25° C. In some embodiments, the chromatographic media and/or supporting equipment is exposed to the solution at a temperature from about 0° C. to about 15° C. In some embodiments, the chromatographic media and/or supporting equipment is exposed to the solution at a temperature from about 0° C. to about 10° C. In some embodiments, the temperature is about 0° C., about 5° C., about 10° C., about 15° C., about 20° C., about 25° C. about 30° C., about 35° C., or about 40° C. In some embodiments, the temperature is about 20° C. In some embodiments, the temperature is about 4° C.

In some embodiments, the present disclosure relates to a method of sanitizing or sterilizing chromatographic media and/or supporting equipment by contacting the media and/or supporting equipment with a solution comprising about 65 mM acetic acid and about 20% hexylene glycol, about pH 3, for at least about 1 hour at a temperature of about 20° C. In some embodiments, the present disclosure relates to a method of sanitizing or sterilizing chromatographic media and/or supporting equipment by contacting the media and/or supporting equipment with a solution comprising about 65 mM acetic acid and about 20% hexylene about pH 3, for at least about 40 minutes at a temperature of about 20° C.

By way of example, and not limitation, in some embodiments, chromatographic media refers to any material packed into a column. In some embodiments, the material is resin or a particle. In some embodiments, the resin is a polymeric support or base matrix. In some embodiments, the polymeric support or base matrix is coupled to an affinity ligand. In some embodiments, the polymeric support or the base matrix may comprise, without limitation, agarose, cellulose, sepharose, polymethacrylate, or polyvinylether. In some embodiments, the chromatographic media is designed for use in immobilized metal affinity chromatography (MAC), ion exchange chromatography (IEX), e.g., cation exchange chromatography (CEX) or anion exchange chromatography (AEX), gel filtration chromatography (also known as size-exclusion chromatography (SEC)), hydrophobic interaction chromatography (HIC), supercritical fluid chromatography (SFC), high performance liquid chromatography (HPLC), ultra-high performance liquid chromatography (UHPLC), high turbulence liquid chromatography (HTLC), normal phase chromatography (NPC), reverse phase chromatography (RPC), capillary liquid chromatography, electrochromatography, membrane chromatography, monolith chromatography, and nano or capillary liquid chromatography.

By way of example, and not limitation, in some embodiments, supporting equipment is one or more select from chromatographic columns, pumps, injectors, interconnecting tubing, detectors, sample collectors, mixers, flow restrictors, inline filters, valves, bubble traps, and ail other liquid contact surfaces.

In some embodiments, the present technology does not impair the function of the chromatography resin or abridge the lifetime performance of the resin. Additionally, or alternatively, in some embodiments, the sanitization or sterilization solution of the present disclosure has low toxicity, is non-flammable, does not cause protein aggregation, and/or is gentle to peptide affinity ligands. In some embodiments, the sanitization or sterilization solution of the present disclosure penetrates biofilms. In some embodiments, the sanitization or sterilization solution of the present disclosure has high wettability, wherein the high wettablity allows for efficient distribution throughout the chromatography media itself, i.e., chromatography beads and bead pores.

Sample Preparation

In some embodiments, the present technology can be applied toward the purification and/or detection of one or more analytes of interest from any source sample, such as biological samples or environmental samples. In some embodiments, the biological sample may be from humans, animals, plants, microorganisms, or any living organelles, such as cell and tissue cultures, tissue biopsy, whole blood, dry blood spot, plasma, de-proteinated plasma, serum, de-proteinated serum, ascites fluid, semen, sputum, urine, feces, perspiration, saliva, bile, tears, cerebrospinal fluid, swabs from body sites, skin, and hair. In some embodiments, the environmental sample may be an air sample, soil sample, water sample, food sample, and any material sample. In some embodiments, the source sample is obtained from cell cultures. In some embodiments, the source sample is obtained from cell culture supernatants. In some embodiments, the source sample is obtained from cell lysates.

In some embodiments, analytes of interest may be, for example, small molecules such as drug substances and macromolecules such as polypeptides, peptides, nucleic acids, lipids or fatty acids, carbohydrates, lipoproteins, lipopolysaccharides (e.g., endotoxins), hormones, vitamins, steroids, and metabolites. In some embodiments, the analyte of interest is a polypeptide. In some embodiments, the polypeptide is a therapeutic polypeptide. In some embodiments, the polypeptide is an enzyme or a recombinant enzyme. In some embodiments, the recombinant enzyme is a human recombinant enzyme. By way of example, and not limitation, in some embodiments, the recombinant enzyme is a lysosomal glycogen-specific enzyme, human enzyme acid α-glucosidase (GAA), alglucosidase alfa, avalglucosidase alfa (neoGAA), Myozyme®, Lumizyme®, Fabrazyme®, Cerezyme®, tissue plasminogen activator (tPA), factor VIII (FVIII), factor IX (FIX), or acid sphingomyelinase (ASM). In some embodiments, the polypeptide is a non-enzymatic protein, e.g., a structural protein (e.g., collagen), a transport protein (e.g., hemoglobin), a regulatory protein (e.g., peptide hormones), a motor protein (e.g., myosin), or an immune protein (e.g., antibodies). In some embodiments, the polypeptide is an antibody, e.g., a monoclonal antibody (mAb), a polyclonal antibody (pAb), a bispecific antibody (BsAb), a trispecific antibody (TsAb), an antigen binding fragment thereof, or an antibody fusion protein. In some embodiments, the antibody is a recombinant monoclonal antibody. The term "antigen-binding fragment" as used herein refers to one or more fragments of an antibody that retain the ability to specifically bind to the same antigen as the whole antibody from which the portion is derived. Examples of "antigen-binding fragment" include, without limitation, a Fab fragment, a F(ab')2 fragment, a Fd fragment, a Fv fragment, a dAb fragment, an isolated complementarity determining region (CDR), scFv, and a diabody.

In some embodiments, majority of contaminants and interfering materials are removed before applying the chromatography method to the source sample. In some embodiments, analytes of interest are enriched and isolated by filtration, precipitation, centrifugation, extraction, dilution, or a combination thereof. In some embodiments, analytes of interest are enriched from a source sample by solid phase extraction (SPE). SPE enriches analytes of interest by using sample preparation cartridges. The SPE extract containing the analytes may be dried and reconstituted in a solvent system compatible with the chromatography system.

In some embodiments, analytes of interest are extracted from a source sample by liquid-liquid extraction (LLE). LLE is used to separate analytes based on their relative solubilities in two immiscible or partially miscible liquids, usually a polar solvent like water and a non-polar organic solvent. The target analyte is first partitioned by a solvent, after which it is extracted, concentrated, and diluted.

In some embodiments, analytes of interest are extracted from a source sample by solid supported liquid-liquid extraction (SLE). In SLE, an aqueous solution of the source sample is loaded onto a support comprising of diatomaceous earth. Following sample absorption into the support, it is washed several times with an organic extraction solvent such as methyl tert-butyl ether. After the analyte of interest has been partitioned into the organic phase, it is concentrated by drying before being reconstituted in a solvent compatible for the chromatography system.

In some embodiments, wherein analytes of interest are proteins, they are enriched from the source sample by protein precipitation extraction (PPE). Protein precipitation methods may include desalting, isoelectric point precipitation, and organic solvent extraction. By way of example, the source sample is prepared for loading into chromatography system by desalting. This protein precipitation technique relies on the protein being "salted out" of the solution in response to increasing concentration of a neutral salt such as ammonium sulfate. In some embodiments, the source sample is prepared by isoelectric point precipitation; this method may be used to precipitate contaminant proteins, rather than the target protein. The isoelectric point (pI) is the pH at which the net primary charge of a protein becomes zero. For most proteins, the pI lies in the pH range of 4 to 6. In some embodiments, inorganic acids such as hydrochloric acid and sulfuric acid are used as precipitants. A potential disadvantage to isoelectric point precipitation is the irreversible denaturation caused by the inorganic acids.

Chromatography

In some embodiments, once the source sample has been processed by, e.g., by centrifugation and/or filtration, the clarified sample is loaded into the chromatography system, e.g., a liquid chromatography system.

Liquid chromatography (LC) is a process of selectively retaining one or more components of a fluid solution as the fluid solution (mobile phase) permeates through a column of a finely divided substance (stationary phase) by pumping action, pressure, and or gravity to accomplish diffusion in and through the pores of the chromatography media. The retention of selective components in the fluid solution by the stationary phase results from the higher affinities of the components for the stationary phase than for the mobile phase. In some embodiments, the liquid chromatography used is affinity chromatography (AC), ion exchange chromatography (IEX), size-exclusion chromatography (SEC), supercritical fluid chromatography (SFC), high performance liquid chromatography (HPLC), ultra-high performance liquid chromatography (UHPLC), high turbulence liquid chromatography (HTLC), normal phase chromatography (NPC), reverse phase chromatography (RPC), capillary liquid chromatography, electrochromatography, membrane chromatography, monolith chromatography, nano or capillary liquid chromatography. In some embodiments, the liquid chromatography system used in this technology is affinity chromatography (AC).

In some embodiments, analytes of interest are retained by the stationary phase and subsequently eluted. In some embodiments, analytes of interest are flow through the stationary phase without being retained. In some embodiments, analytes in the eluate or in the effluent are be monitored by a variety of means, including UV, fluorescence, refractive index, light scattering, and electrical conductivity, based on retention time, peak intensity, and peak area. In some embodiments, further detailed analysis of the analytes is performed with techniques such as mass spectrometry.

In some embodiments, the LC solvents include, without limitation, water, methanol, ethanol, acetonitrile, trifluoroacetic acid, heptafluorobutyric acid, ether, hexane, hexylene glycol, ethyl acetate, and an organic solvent such as hydrocarbon solvents (e.g., aliphatic and aromatic solvents), oxygenated solvents (e.g., alcohols, glycols, ketones, aldehydes, glycol ethers, esters, and glycol ether esters), and halogenated solvents (e.g., chlorinated and brominated hydrocarbons). In some embodiments, the LC solvents are buffered, and may contain various salts and buffering agents routinely used in the art, e.g., sodium acetate, ammonium acetate, ammonium formate, ammonium bicarbonate, acetic acid, trifluoroacetic acid, formic acid, trimethylamine, triethylamine, etc. In some embodiments, the LC solvents also include detergents such as Tween, SDS, etc.

Affinity Chromatography (AC)

In some embodiments, the liquid chromatography used is affinity chromatography. Affinity chromatography utilizes specific biological interactions between molecules. Types of biological interactions commonly exploited in affinity chromatography include, without limitation, antigen-antibody interaction, protein-immunoglobulin interaction, enzyme-substrate/cofactor/inhibitor interaction, nucleic acid-nucleic acid binding protein interaction, lectin-polysaccharide/glycoprotein interaction, avidin-biotin interaction, calmodulin-calmodulin binding partner interaction, glutathione-GST fusion protein interaction, metal ion-poly-histidine fusion protein interaction, and receptor-hormone interaction.

In some embodiments, a biospecific ligand (affinity ligand) is chemically immobilized onto a solid support (e.g., cellulose, agarose, or polyacrylamide) within a column so that when a crude extract is passed over the column, those molecules having specific binding affinity to the ligand (target analytes) become adsorbed. After other contaminants are washed away, the bound analyte is eluted from the support, resulting in its purification from the original sample. In some embodiments, the affinity chromatography used is immunoaffinity chromatography (IAC), protein A, protein G, or protein L affinity chromatography, lectin affinity chromatography, dye-ligand affinity chromatography, immobilized metal affinity chromatography (IMAC), or boronate affinity chromatography. In some embodiments, the affinity chromatography used is protein A chromatography.

Affinity chromatography resins comprise a polymeric support with a chemically coupled affinity ligand. Affinity ligands include biological and synthetic ligands. In some embodiments, the affinity ligand is a biological ligand, e.g., peptides, polypeptides (proteins), nucleotides, oligonucleotides (nucleic acids), coenzymes, vitamins, lectins, and antibodies. In some embodiments, the affinity ligand is a synthetic ligand. Synthetic ligands are generated either by de novo synthesis or modification of existing molecular structures (e.g., triaznyl nucleotide-mimetics, purine and pyrimidine derivatives, non-natural peptides, triazinyl dyes, other triazine-based ligands, oligosaccharides, and boronic acid analogues).

In some embodiments, the affinity ligand binds to a peptide, a small molecule, a protein, or an enzyme. In some embodiments, the enzyme is a recombinant enzyme. In some embodiments, the recombinant enzyme is a human recombinant enzyme. By way of example, and not limitation, in some embodiments, the recombinant enzyme is a lysosomal glycogen-specific enzyme, human enzyme acid α-glucosidase (GAA), alglucosidase alfa, avalglucosidase alfa (neoGAA), Myozyme®, Lumizyme®, Fabrazyme®, Cerezyme®, tissue plasminogen activator (tPA), factor VIII (FVIII), factor IX (FIX), or acid sphingomyelinase (ASM).

In some embodiments, the affinity ligand is based on Protein A or a variant thereof. In some embodiments, the affinity ligand is based on Protein G or a variant thereof. In some embodiments, the affinity ligand is based on Protein A/G or a variant thereof. In some embodiments, the affinity ligand is based on Protein L or a variant thereof.

Protein A Affinity Chromatography

Protein A affinity chromatography is widely used for the purification of monoclonal antibodies (mAbs), polyclonal antibodies (pAbs), antigen-binding fragments thereof, and antibody fusion proteins. It uses a protein A affinity resin comprising a protein A ligand cross-linked to a base matrix as the stationary phase to capture one or more antibodies of interest from the mobile phase. The term "protein A ligand" refers to an affinity ligand based on native protein A or any variant thereof. Staphylococcal protein A (SpA), a 42 kDa cell surface protein, binds to the Fc portion of immunoglobulins (e.g., immunoglobulin G or IgG) using its five homologous immunoglobulin-binding domains (E, D, A, B, and C).

Protein G Affinity Chromatography

Protein G affinity chromatography is widely used for the purification of monoclonal antibodies (mAbs), polyclonal antibodies (pAbs), antigen-binding fragments thereof, and antibody fusion proteins. It uses a protein G affinity resin comprising a protein G ligand cross-linked to a base matrix as the stationary phase to capture one or more antibodies of interest from the mobile phase. The term "protein G ligand" refers to an affinity ligand based on native protein G or any variant thereof. Streptococcal protein G, a cell wall protein comprising two (or three) GA domains and two (or three) B domains, binds to the Fc as well as Fab portions of immunoglobulins (e.g., immunoglobulin G or IgG). However, the interaction between protein G and Fab is much weaker than its interaction with Fc.

Protein A/G Affinity Chromatography

Protein A/G affinity chromatography is widely used for the purification of monoclonal antibodies (mAbs), polyclonal antibodies (pAbs), antigen-binding fragments thereof, and antibody fusion proteins. It uses a protein A/G affinity resin comprising a protein A/G ligand cross-linked to a base matrix as the stationary phase to capture one or more antibodies of interest from the mobile phase. The term "protein A/G ligand" refers to an affinity ligand based on recombinant protein A/G or any variant thereof. Protein A/G is a ~51 kDa recombinant fusion protein that combines the antibody binding domains of Staphylococcal Protein A and Streptococcal Protein G. Protein A/G contains four Fc binding domains from Protein A and two Fc binding domains from Protein G. Protein A/G is used to purify polyclonal or monoclonal antibodies from various species.

Protein L Affinity Chromatography

Protein L affinity chromatography is widely used for the purification of monoclonal antibodies (mAbs), polyclonal antibodies (pAbs), antigen-binding fragments thereof, and antibody fusion proteins. It uses a protein L affinity resin comprising a protein L ligand cross-linked to a base matrix as the stationary phase to capture one or more antibodies of interest from the mobile phase. Protein L is a ~95 kDa cell surface immunoglobulin binding protein originally isolated from *Peptococcus magnus*. The term "protein L ligand" refers to an affinity ligand based on recombinant protein L or any variant thereof recombinantly expressed in *Escherichia coli* or any other non-native host cell.

Target Analyte Purification Method

In some embodiments, the present disclosure relates to the purification of macromolecular analytes (e.g., antibodies, enzymes, hormones, growth factors, DNA/RNA, lectins, therapeutic non-enveloped viruses, etc.) from cell cultures. In some embodiments, the target analyte is an antibody, wherein the purification process comprises the following steps:

(i) Sanitization—All chromatography media and supporting equipment are pre-sanitized with the AAH sanitization solution, wherein the sanitization method comprises contacting the media and the equipment with the AAH sanitization solution at 0-40° C., preferably 15-25° C., for at least 1 hour.

(ii) Harvesting—Cells, cell debris, and other impurities are separated from the cell culture supernatant by conducting centrifugation, depth filtration, microfiltration, and/or alternative tangential flow.

(ii) Affinity Chromatography—The target antibody is captured from the cell culture supernatant at neutral pH on a pre-sanitized, equilibrated affinity chromatography resin, washed, and eluted at an acidic pH.

(iii) Viral inactivation—Low pH retrovirus inactivation is usually conducted at low pH (3.3-3.6) for ≥60 minutes hold time if the target antibody is stable at the test pH.

(iv) Cation exchange chromatography (CEX)—Host cell proteins (HCPs), antibody aggregates, and antibody fragments are removed by passing the sample through a pre-sanitized cation exchange column.

(v) Anion exchange chromatography (AEX)—DNA, any leached Protein A, and other trace contaminants are removed by passing the sample through a pre-sanitized anion exchange column.

(vi) Small viral retentive filtration—The sample is subjected to a viral clearance step to remove any contaminant viruses.

(vii) Ultrafiltration—The target antibody is concentrated to a desired concentration and buffer exchanged into a desired formulation buffer.

In some embodiments, the target antibody is captured from the cell culture supernatant on a protein A affinity chromatography resin comprising a protein A ligand chemically conjugated to a polymeric support, beaded or membrane. In some embodiments, the protein A ligand is based on natural protein A. In some other embodiments, the protein A ligand is based on artificial protein A. For instance, an artificial protein A may comprise a non-natural amino acid residue. In some embodiments, the protein A ligand is based on native protein A extracted from *Staphyloccocus aureus*. In some other embodiments, the protein A ligand is based on protein A, or any variant thereof, recombinantly expressed in *Escherichia coli* or *Brevibacillus choshinensis*. In some embodiments, the protein A ligand is based on genetically engineered protein A (e.g., alkaline resistant protein A or protein A variants containing repeat units derived from the B or C domain). In some embodiments, the protein A ligand is based on mutant protein A (e.g., protein A variants containing point mutations in the B and C domains). In some embodiments, the protein A ligand is based on truncated protein A.

In some embodiments, the target antibody is captured from the cell culture supernatant on a protein G affinity chromatography resin comprising a protein G ligand chemically conjugated to a polymeric support. In some embodiments, the protein G ligand is based on natural Protein G. In some other embodiments, the protein G ligand is based on artificial Protein G. For instance, an artificial protein G may comprise a non-natural amino acid residue. In some other embodiments, the protein G ligand is based on native protein G isolated from group C or group G streptococci. In some embodiments, the protein G ligand is based on protein G, or any variant thereof, recombinantly expressed in *Escherichia coli*. In some embodiments, the protein G ligand is based on genetically engineered Protein G (e.g., nonalbumin-binding forms of protein G). In some embodiments, the protein G ligand is based on mutant Protein G. In some embodiments, the protein G ligand is based on truncated Protein G.

In some embodiments, the target antibody is captured from the cell culture supernatant on a protein A/G affinity chromatography resin comprising a protein A/G ligand chemically conjugated to a polymeric support. In some embodiments, the protein A/G ligand is based on protein A/G, or any variant thereof, recombinantly expressed in *Escherichia coli*. In some embodiments, the protein A/G ligand is based on genetically engineered protein A/G. In some embodiments, the protein A/G ligand is based on mutant protein A/G. In some embodiments, the protein A/G ligand is based on truncated protein A/G. In some embodiments, the protein A/G ligand is based on artificial protein A/G.

In some embodiments, the target antibody is captured from the cell culture supernatant on a protein L affinity chromatography resin comprising a protein L ligand chemically conjugated to a polymeric support. In some embodiments, the protein L ligand is based on natural protein L. In some other embodiments, the protein L ligand is based on artificial protein L. For instance, an artificial protein L may comprise a non-natural amino acid residue. In some other embodiments, the protein L ligand is based on native protein L isolated from *Peptococcus magnus*. In some embodiments, the protein L ligand is based on protein L, or any variant thereof, recombinantly expressed in *Escherichia coli*. In some embodiments, the protein L ligand is based on genetically engineered protein L. In some embodiments, the protein L ligand is based on mutant protein L. In some embodiments, the protein L ligand is based on truncated protein L.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to the manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. Although a number of documents are cited herein, this citation does not constitute an admission that any of these documents forms part of the common general knowledge in the art.

Chromatography Buffer

In some embodiments, the present technology relates to a chromatography buffer solution comprising a carboxylic acid and a glycol. In some embodiments, the chromatography buffer is a wash buffer that can be used to wash unbound or loosely bound (e.g., via non-specific interactions) proteins and/or other contaminants from the surface of the chromatography media. In some embodiments, the chromatography buffer is an elution buffer that can be used to remove the bound target analyte (e.g., antigens, antibodies, enzymes, etc.) from the surface of the chromatography media.

In some embodiments, the present technology relates to an elution buffer or wash buffer comprising acetic acid. In some embodiments, the buffer comprises about 40-200 mM acetic acid. In some embodiments, the buffer comprises about 40-200 mM, about 50-190 mM, about 60-180 mM, about 70-170 mM, about 80-160 mM, about 90-150 mM, about 100-140 mM, or about 110-130 mM acetic acid. In some embodiments, the buffer comprises about 40, 50, 60, 70, 80, 90, 100, 110, 120, 130, 140, or 150 (or any number between any two of the preceding values) mM acetic acid. In some embodiments, the buffer comprises about 65 mM acetic acid.

In some embodiments, the present technology relates to an elution buffer or wash buffer comprising hexylene glycol. In some embodiments, the buffer comprises about 8-80% hexylene glycol. In some embodiments, the buffer comprises about 10-70%, about 12-60%, about 14-50%, about 16-40%, about 18-30%, or about 20-25% hexylene glycol. In some embodiments, the buffer comprises about 8%, 10%, 12%, 14%, 16%, 18%, 20%, 25%, 30%, 40%, 50%, 60%, 70%, or 80% hexylene glycol. In some embodiments, the buffer comprises about 20% hexylene glycol.

In some embodiments, the present technology relates to an elution buffer or wash buffer comprising acetic acid and hexylene glycol. In some embodiments, the present technology relates to an elution buffer comprising about 40-200 mM acetic acid and about 8-80% hexylene glycol, about 50-190 mM acetic acid and about 10-70% hexylene glycol, about 60-180 mM acetic acid and about 12-60% hexylene glycol, about 70-170 mM acetic acid and about 14-50% hexylene glycol, about 80-160 mM acetic acid and about 16-40% hexylene glycol, about 90-150 mM acetic acid and about 18-30% hexylene glycol, about 100-140 mM acetic acid and about 20-25% hexylene glycol, or about 110-130 mM acetic acid and about 20-25% hexylene glycol.

In some embodiments, the present technology relates to an elution buffer or wash buffer comprising about 40 mM acetic acid and about 8% hexylene glycol, about 50 mM acetic acid and about 10% hexylene glycol, about 60 mM acetic acid and about 12% hexylene glycol, about 70 mM acetic acid and about 14% hexylene glycol, about 80 mM acetic acid and about 16% hexylene glycol, about 90 mM acetic acid and about 18% hexylene glycol, about 100 mM acetic acid and about 20% hexylene glycol, about 110 mM acetic acid and about 25% hexylene glycol, about 120 mM acetic acid and about 30% hexylene glycol, about 130 mM acetic acid and about 40% hexylene glycol, about 140 mM acetic acid and about 50% hexylene glycol, about 150 mM acetic acid and about 60% hexylene glycol, about 160 mM acetic acid and about 70% hexylene glycol, about 170 mM acetic acid and about 80% hexylene glycol, about 180 mM acetic acid and about 80% hexylene glycol, about 190 mM acetic acid and about 80% hexylene glycol, or about 200 mM acetic acid and about 80% hexylene glycol. In some embodiments, the present technology relates to an elution buffer comprising about 65 mM acetic acid and about 20% hexylene glycol.

In some embodiments, the present technology relates to an elution buffer or wash buffer with a pH of about 3.5. In some embodiments, the buffer has a pH of about 3.4, about 3.3, about 3.2, or about 3.1, about 3.0, or about 2.9. In some embodiments, the buffer has a pH of about 3.0.

In some embodiments, the elution buffer or wash buffer comprises about 65 mM acetic acid and about 20% hexylene glycol and has about a pH of about 3.0.

EXAMPLES

In order that this technology may be better understood, the following examples are set forth. These examples are for purposes of illustration only and are not to be construed as limiting the scope of the technology in any manner.

Example 1

Study to Evaluate the Impact of Sanitization Methods on Resin Stability

This example describes a batch bind study to evaluate the initial and continued impact of various sanitization methods on the functionality and longevity/durability of chromatographic media.

Methods

Chemicals & Reagents

The chromatography media comprises an affinity ligand chemically cross-linked by epoxy bond to an agarose base matrix.

Time-Course Assay

The time-course was established by buffer exchanging a source pool of chromatography resin into a 50% slurry under desired sanitization conditions, including treatment with sanitization buffers and exposure to gamma radiation. The compositions of various sanitization buffers used in this study are described in Table 1 below. At specified times, 1 mL of the resin was removed from the source pool, buffer exchanged into equilibration buffer, and then mixed with alglucosidase alfa drug substance to test binding at a target binding capacity of 15 mg/mL resin. The binding capacity of the resin at set timepoints was normalized against the binding capacity at T0 and plotted across the time course (FIG. 1). Gamma irradiated resin was only evaluated at T0 and compared to naïve resin as irradiation was a single exposure to a dose of 2, 7, or 25 kGy/hr gamma irradiation.

Methods

To explore the impact of sanitization methods on the lifetime of the resin, cycling studies were performed. Under continuous operation conditions, a 1 cm column was cycled 25 times after gamma irradiation to 25 kGy at T0. Additionally, a 0.66 cm column was cycled 100 times after treatment with sanitization buffers comprising sodium hydroxide and/or tween at T0.

Results

The cycling of the gamma irradiated columns displayed a 50% reduction in binding capacity when compared to the naïve virgin resin. Cycling for the gamma-irradiated resin was stopped at 25 cycles due to rapid decline in column performance suggesting severe structural damage to the resin itself.

Figure 2:
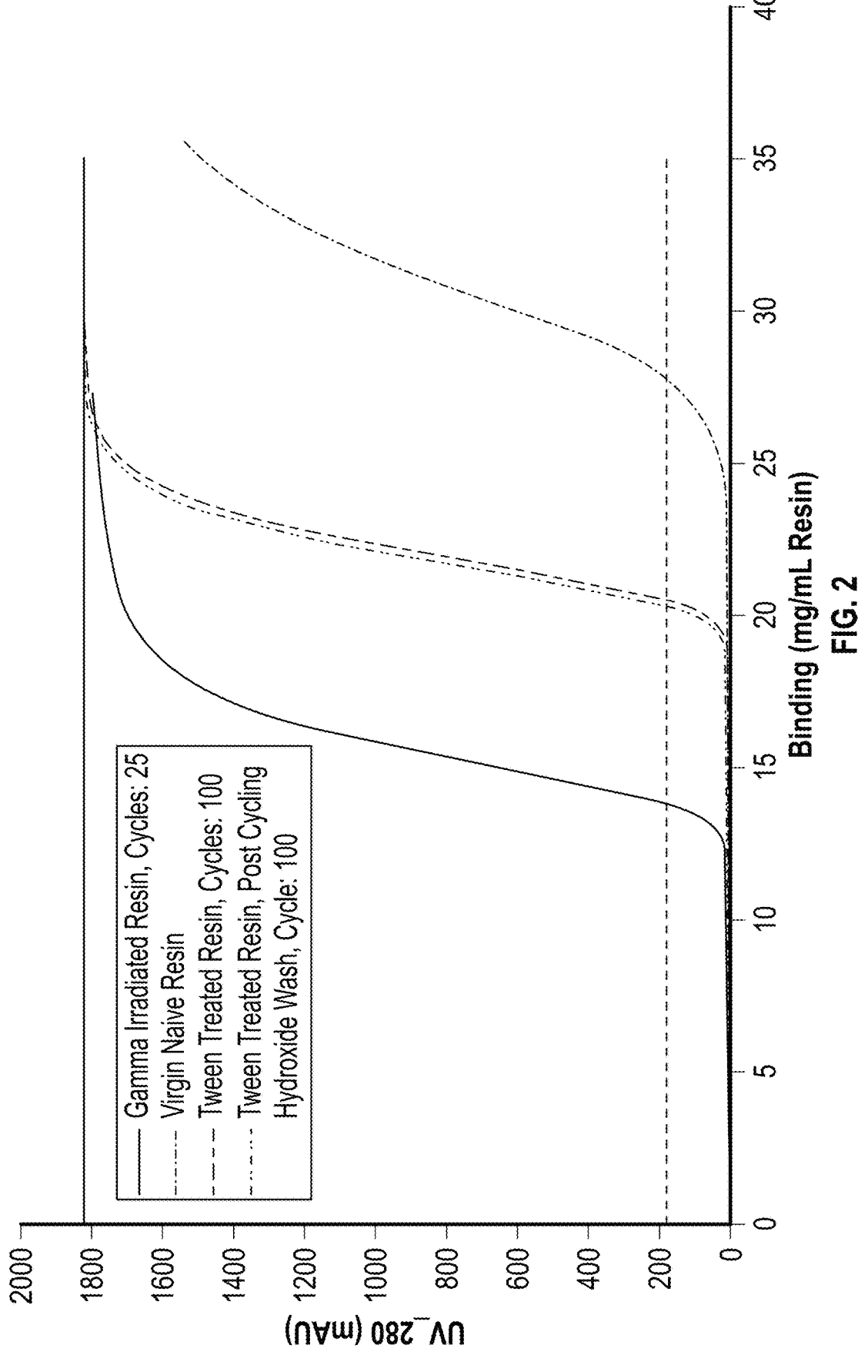
FIG. 2 is a plot depicting the impact of various sanitization methods on resin lifetime.

The cycling of the tween treated resin displayed a 23% reduction in binding capacity when compared to the naïve virgin resin. The resin was cycled 100 times to represent the expected lifetime of an affinity ligand. The 23% reduction in binding capacity is likely attributed in part to the loss in column performance across a long lifetime but also attributed to hydroxide exposure. Minimal hydroxide exposure was explored in this lifetime study to extend resin life. Any increase in hydroxide exposure would further decrease binding capacity. The dynamic binding capacity (DBC) of the columns after cycling is shown in FIG. 2.

TABLE 1

| Buffer No. | Acetic Acid | Phosphoric Acid | Sodium Acetate | Sodium Hydroxide | Benzyl Alcohol | Tween |
|---|---|---|---|---|---|---|
| 1 (PAT) | 150 mM | 100 mM | — | — | — | 5% |
| 2 (PAB) | 167 mM | 120 mM | — | — | 2.2% | — |
| 3 (PA) | 150 mM | 100 mM | — | — | — | — |
| 4 (control) | — | — | 100 mM | — | — | — |
| 5 | — | — | — | 0.1M | — | 5% |
| 6 | — | — | — | 0.5M | — | — |

Results

This study revealed that exposure to gamma irradiation resulted in an initial 20% drop in binding capacity of the resin. Further, long term exposure of the affinity ligand to sodium hydroxide buffers resulted in binding capacity drops of 20% or more depending on the duration of exposure and the concentration of sodium hydroxide. Surprisingly, the affinity ligand was much more stable in acidic buffers (pH=1.7) and displayed comparable maintenance of binding capacity across the entire time course to the control (100 mM sodium acetate, pH 5.6).

Example 2

Study to Evaluate the Impact of Sanitization Methods on Resin Lifetime

This Example describes a cycling study to evaluate the impact of various sanitization methods on the lifetime performance of chromatographic media.

Example 3

Study to Evaluate the Impact of AAH Sanitization Buffer on Resin Lifetime

This Example describes a pilot scale study to evaluate the impact of a sanitization buffer comprising acetic acid and hexylene glycol on the lifetime performance of chromatography media.

Methods

To explore the impact of a sanitization buffer comprising 65 mM acetic acid and 20% hexylene glycol (AAH sanitization buffer) on the lifetime performance of affinity chromatography resins, two pilot scale studies were performed. Briefly, the resin performance of a 10 cm column was evaluated after it was cycled 70 times, such that in each cycle the column was exposed to 2CV of the sanitization buffer (~40 min/cycle).

Results

Figure 3A:
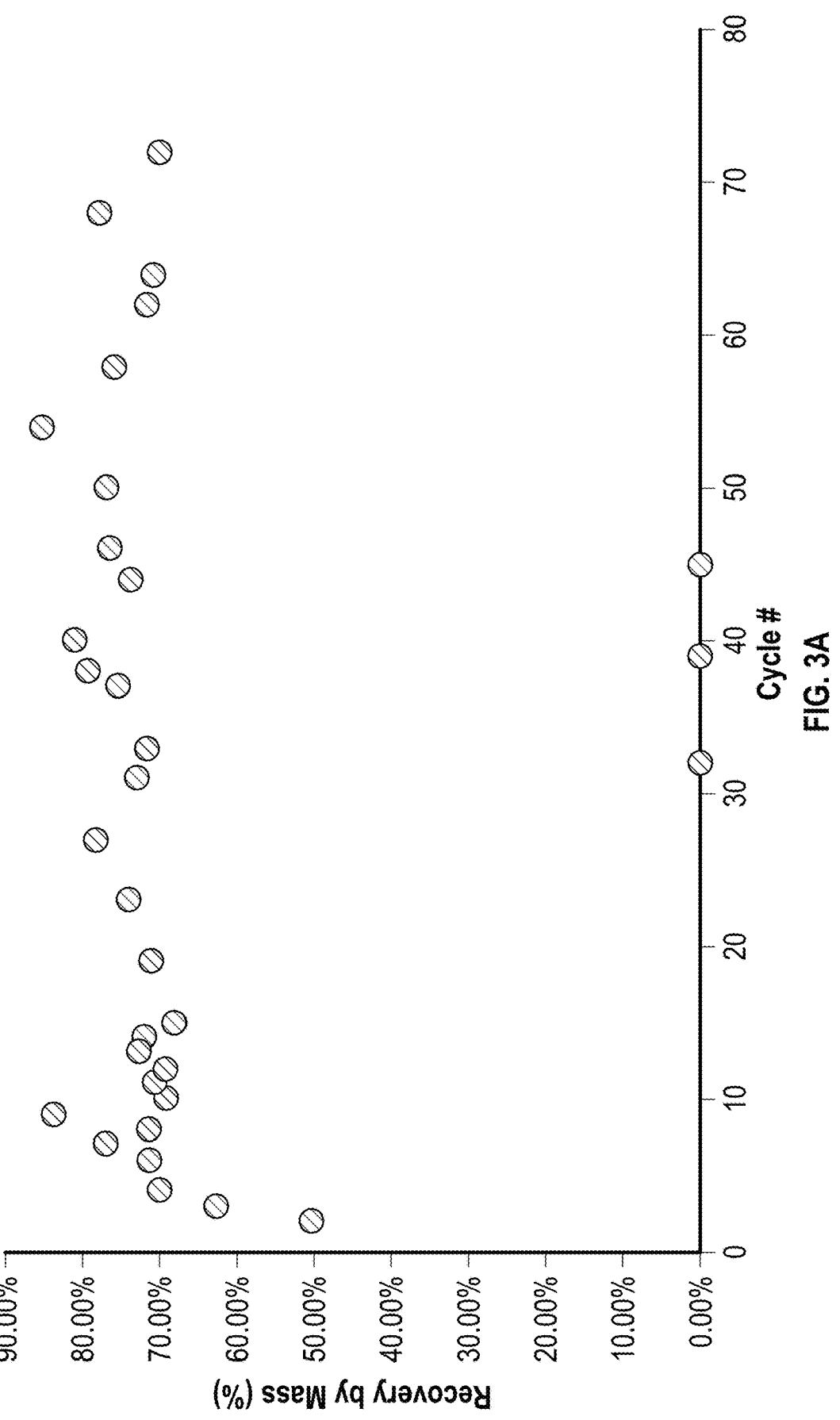
FIGS. 3A and 3B are plots depicting the impact of a solution comprising 65 mM acetic acid and 20% hexylene glycol (AAH sanitization solution) on resin lifetime.
Figure 3B:
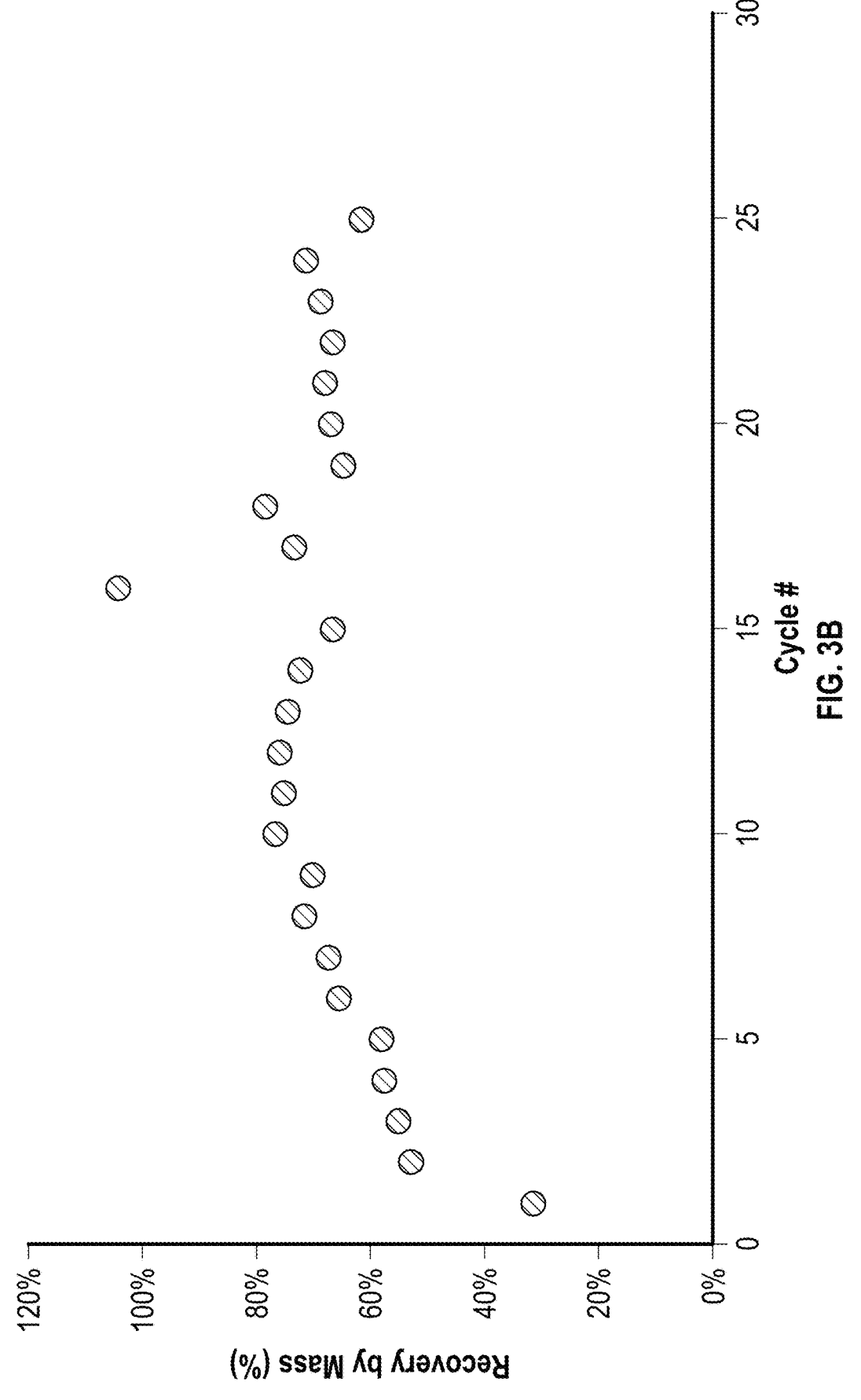

There was no change in recovery after exposure to the AAH sanitization buffer for up to 46 hours (in the case of 70 cycles) when operating at setpoint conditions. This study indicated that the AAH sanitization buffer did not have a detrimental impact on the lifetime performance of the affinity ligand (FIGS. 3A and 3B).

This data shows that a solution of the present technology comprising acetic acid and hexylene glycol does not impair the function of an affinity ligand. Accordingly, the solution of the present technology is useful in sanitization or sterilization methods for sanitizing, regenerating, and/or sterilizing chromatography media and/or supporting equipment.

Example 4

Study to Evaluate the Microbicidal Efficacy of AAH Sanitization Solution

This Example describes a microbial kill study to evaluate the microbicidal efficacy of a sanitization solution comprising acetic acid and hexylene glycol.

Methods

A screening batch kill study was performed using the AAH sanitization solution as well as other potential sanitization solutions. Briefly, a microorganism spiking solution ($10^8$ cells/mL) was prepared. These microorganisms included *E. Coli* (ATCC 10536; gram negative), *S. Aureus* (ATCC 6538; gram positive), *O. Anthropi* (house isolate; gram negative), *B. Cereus* (house isolate; gram negative) and *B. Thuringiensis* (house isolate; spore forming). Different tubes containing different sanitization solutions were spiked and sampled after predefined time points (T20, T40, T60, and T24h). The samples were then analyzed for bioburden concentration and results were converted to logarithmic values. Log10 reductions were calculated based on a T0 PBS control.

Further, a pilot scale study was performed to detect the presence of endotoxins in sample eluates. Briefly, a 10 cm column was operated as an open system and treated with 2CV of AAH sanitization solution every cycle over the course of 73 cycles. As part of operation, every 4 column cycles were pooled into a single eluate (usually over the course of 24 hours). Endotoxin was measured using Charles River Endosafe nexgen-PTS endotoxin testing kit. Beyond sampling eluate for endotoxin, after completion of life cycle, the end of life (EoL) resin was exchanged into equilibration buffer (100 mM Sodium Acetate, pH 5.6) and was held for 1 week at room temperature. At the end of hold, effluent was tested for endotoxin.

Results

FIG. 4 shows the microbicidal effectiveness of the AAH sanitization solution at killing several representative bacteria, spores, and/or mold compared to sodium hydroxide and other acid sanitants. As per FIG. 4, the AAH sanitization solution was the only solution to achieve complete kill of all species tested in less than 1 hour. Caustic sanitants such as 0.5M NaOH were not effective against spore forming microbial contaminants. This complete kill in less than 1 hour proves that the AAH sanitization solution is surprisingly superior to a current protein A acid sanitant (2% PAB; Merck-Millipore) which operates at harsher conditions (pH 1.7) and takes a minimum of 10 hours to kill tested spore forming species at slightly reduced temperatures. Thus, AAH sanitization solution killed all tested microbial species in surprisingly less time (less than 1 hour) and under much milder conditions. No endotoxin was detected in any of the tested eluate samples (all endotoxin levels were returned as below the limit of detection. This suggests that the present sanitization method achieved control over gram negative bacteria. This data shows that a solution of the present technology comprising acetic acid and hexylene glycol has microbicidal properties. Accordingly, the solution of the present technology is useful in methods of sanitizing or sterilizing chromatography media and/or supporting equipment.

Example 5

Study to Evaluate the Elution Efficiency of the AAH Solution

This Example describes two studies to evaluate the elution efficiency of a solution comprising acetic acid and hexylene glycol.

Methods

To explore the elution efficiency of a buffer comprising acetic acid and a glycol (e.g., hexylene glycol), various elution buffer formulations were tested. The compositions of the elution buffers used in this study, the eluate protein concentrations, and activity recoveries of the target analyte are described in Table 2 below. The target analyte used in this study was Myozyme®. Additionally, a second study was performed to compare the effect of ethylene glycol vs. hexylene glycol on the elution efficiency of the elution buffer. An elution buffer comprising no glycol was used as a control in this study.

Results

Figure 5:
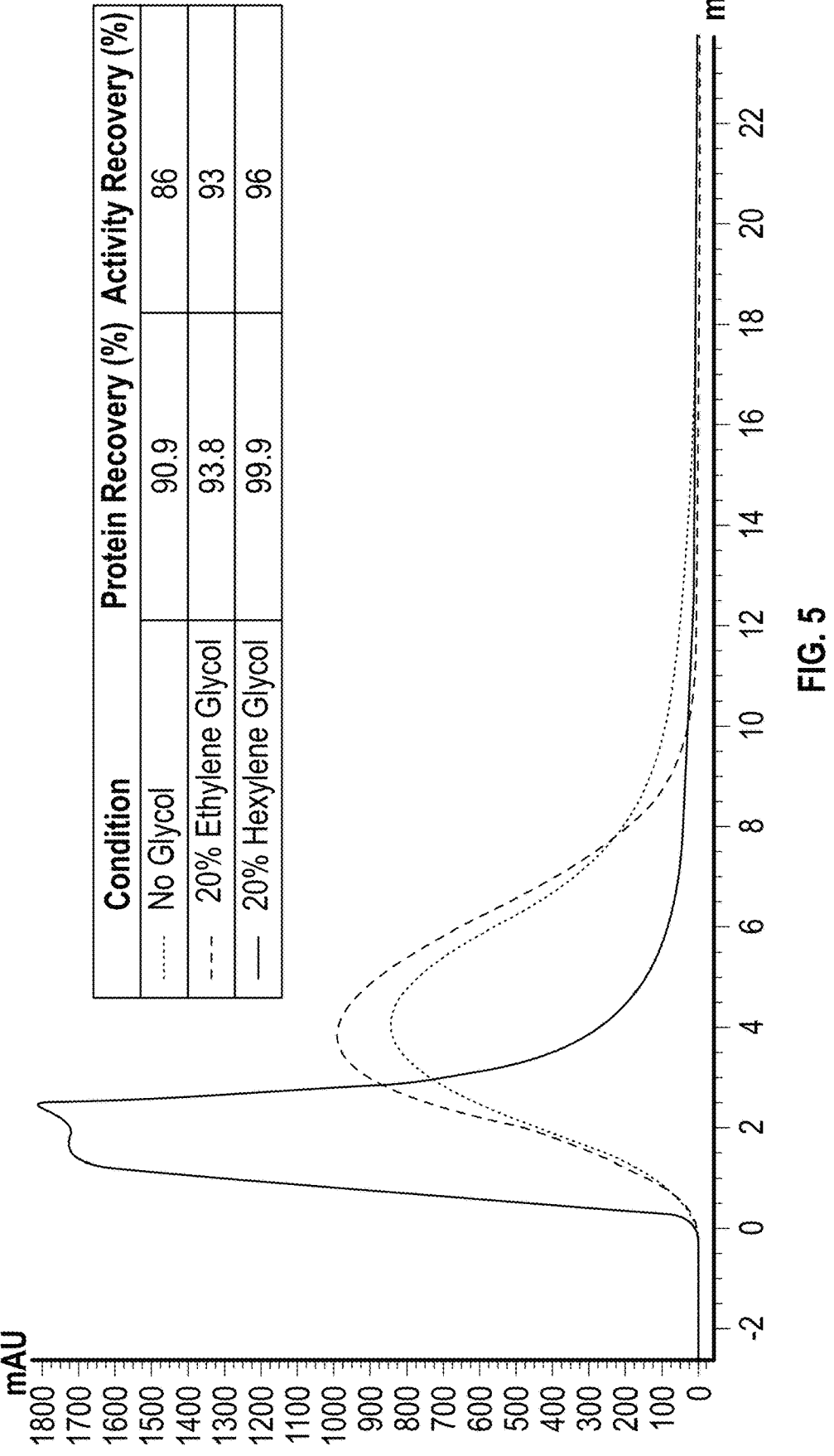
FIG. 5 is a plot depicting the elution profiles of Myozyme® in elution buffers comprising no glycol, 20% ethylene glycol, or 20% hexylene glycol.

As shown in Table 2, all buffer formulations tested in the first study resulted in product elution from the column. FIG. 5 demonstrates that an elution buffer comprising 20% hexylene glycol resulted in better product yield and peak sharpness than an elution buffer comprising no glycol or 20% ethylene glycol.

Thus, a solution comprising acetic acid and hexylene glycol can also serve as an elution buffer. The ability to integrate the AAH solution as a process step coupled with its microbiocidal capabilities further increases its value to bioprocessing.

TABLE 2

| Acetic Acid Concentration (mM) | Hexylene Glycol Concentration (% v/v) | Eluate Protein Concentration (mg/mL) | Recovery by pNP Activity (%) |
|---|---|---|---|
| 40 | 0 | 4.056 | 71 |
| 70 | 0 | 7.414 | 72 |
| 60 | 0 | 6.32 | 73 |
| 65 | 0 | 6.86 | 73 |
| 150 | 0 | 9 | 76 |
| 65 | 10 | 5.423 | 73 |
| 200 | 0 | 12.05 | 78 |
| 65 | 5 | 5.282 | 72 |
| 65 | 20 | 5.19 | 76 |
| 65 | 15 | 5.377 | 74 |
| 100 | 20 | 8.629 | 76 |
| 125 | 20 | 8.501 | 75 |

The invention claimed is:

1. A method for sanitizing or sterilizing chromatography media and/or supporting equipment, comprising contacting the chromatography media and/or supporting equipment with a sanitization or sterilization solution comprising acetic acid and hexylene glycol, wherein the concentration of acetic acid is from about 40 mM to about 200 mM, the concentration of hexylene glycol is from about 8% by volume to about 80% by volume, and the pH of the sanitization or sterilization solution is ≤3.5.

2. A method for eluting a target analyte bound to a chromatography media, comprising contacting the chromatography media with an elution buffer comprising acetic acid and hexylene glycol, wherein the concentration of acetic acid is from about 40 mM to about 200 mM, the concentration of hexylene glycol is from about 8% by volume to about 80% by volume, and the pH of the elution buffer is ≤3.5.

3. The method of claim 1, wherein the concentration of acetic acid is about 65 mM.

4. The method of claim 2, wherein the concentration of acetic acid is about 65 mM.

5. The method of claim 1, wherein the method provides a more effective bacteria, spore, and/or mold inactivation or killing within 1 hour of treatment with the sanitization or sterilization solution as compared to sanitizing or sterilizing the chromatography media and/or supporting equipment with a sanitization or sterilization solution comprising sodium hydroxide.

6. The method of claim 2, wherein the method provides improved product yield and peak sharpness as compared to eluting the target analyte with an elution buffer comprising no glycol or 20% by volume ethylene glycol.

7. The method of claim 1, wherein the concentration of hexylene glycol is about 20% by volume.

8. The method of claim 1, wherein the chromatography media is an affinity chromatography media.

9. The method of claim 8, wherein the affinity chromatography media comprises an affinity ligand that is based on protein A, protein G, protein A/G, or protein L, or any variant thereof.

10. The method of claim 9, wherein the affinity ligand is based on native protein A, recombinant protein A, genetically engineered protein A, or artificial protein A.

11. The method of claim 1, wherein the pH of the sanitization or sterilization solution is from about 3.0 to about 3.5.

12. The method of claim 11, wherein the pH of the sanitization or sterilization solution is about 3.1.

13. The method of claim 5, wherein the bacteria, spore, and/or mold inactivation is achieved within 40 minutes of treatment with the sanitization or sterilization solution.

14. The method of claim 1, wherein the sanitization method is used in a process comprising steps toward the purification of a polypeptide.

15. The method of claim 14, wherein the polypeptide is an antibody or a recombinant enzyme.

16. The method of claim 15, wherein the antibody is a monoclonal antibody.

17. The method of claim 15, wherein the recombinant enzyme is a human recombinant enzyme.

18. The method of claim 15, wherein the recombinant enzyme is a lysosomal glycogen-specific enzyme, a human enzyme acid α-glucosidase (GAA), avalglucosidase alfa or alglucosidase alfa.

19. A method of increasing the lifetime of a chromatography media, comprising sanitizing or sterilizing the chromatography media with a solution comprising about 65 mM acetic acid and about 20% by volume hexylene glycol, wherein the method allows the lifetime of the chromatography media to be increased by at least about 10% as compared to sanitizing or sterilizing the chromatography media with at least one of: (i) gamma irradiation or (ii) a buffer comprising sodium hydroxide.

20. The method of claim 19, wherein the chromatography media comprises at least one of: an affinity resin, a resin that is based on protein A or a variant thereof, and a resin that is based on protein G or a variant thereof.

21. The method of claim 19, wherein the sanitizing or sterilizing comprises a step within an integrated continuous biomanufacturing process for purification of a polypeptide.

* * * * *